US 6,610,740 B1

(12) United States Patent
Wakefield et al.

(10) Patent No.: US 6,610,740 B1
(45) Date of Patent: Aug. 26, 2003

(54) POLYETHYLENE GLYCOL ESTERS OF POLYUNSATURATED FATTY ACIDS

(75) Inventors: Paul Andrew Wakefield, Cumbria (GB); Philip Knowles, Cumbria (GB); Mehar Singh Manku, Cumbria (GB); David Frederick Horrobin, Scotland (GB)

(73) Assignee: Scotia Holdings PLC, Scotland (GB)

( * ) Notice: Subject to any disclaimer, the term of this patent is extended or adjusted under 35 U.S.C. 154(b) by 0 days.

(21) Appl. No.: 09/155,550

(22) PCT Filed: Mar. 19, 1997

(86) PCT No.: PCT/GB97/00765

§ 371 (c)(1),
(2), (4) Date: Nov. 12, 1998

(87) PCT Pub. No.: WO97/35593

PCT Pub. Date: Oct. 2, 1997

(30) Foreign Application Priority Data

Mar. 25, 1996 (GB) ................................... 9606216

(51) Int. Cl.[7] ............................................. A61K 31/765
(52) U.S. Cl. ...................................... 514/549; 523/105
(58) Field of Search ........................... 514/549; 523/105

(56) References Cited

U.S. PATENT DOCUMENTS

| | | | | |
|---|---|---|---|---|
| 3,871,837 A | * | 3/1975 | Bedague et al. | |
| 4,032,304 A | * | 6/1977 | Dorer, Jr. et al. | |
| 4,248,726 A | * | 2/1981 | Uchinuma et al. | |
| 4,364,743 A | * | 12/1982 | Erner | |
| 4,377,667 A | | 3/1983 | Sakurai et al. | |
| 4,816,483 A | | 3/1989 | Georgieva et al. | |
| 5,227,403 A | * | 7/1993 | Seto et al. | 514/549 |
| 5,308,634 A | | 5/1994 | Cooper | |
| 5,376,398 A | | 12/1994 | Cooper et al. | |
| 5,670,540 A | * | 9/1997 | Horrobin et al. | 514/549 |

FOREIGN PATENT DOCUMENTS

| | | |
|---|---|---|
| DE | 31 23 065 | 3/1982 |
| EP | 0 031 310 | 1/1981 |
| GB | 1338385 | 11/1973 |

OTHER PUBLICATIONS

Patent Abstracts of Japan, vol. 013, No. 238 (C–603), Jun. 5, 1989 & JP 01 047701 A (ASAHI Denka Kogyo KK), Feb. 22, 1989, see abstract.
Patent Abstracts of Japan, vol. 012, No. 186 (C–500), May 31, 1988 & JP 62 290740 A (Miyoshi Oil & Fat Co Ltd), Dec. 17, 1987, see abstract.

* cited by examiner

Primary Examiner—Margaret Medley
(74) Attorney, Agent, or Firm—Jacobson Holman PLLC

(57) ABSTRACT

A nutritional, cosmetic or pharmaceutical formulation comprising esters of polyethylene glycol in which the polyethylene glycol chain is terminated at one end by a polyunsaturated fatty acyl group, preferably $C_{18}$–$C_{22}$ and at the other end by a $C_1$–$C_4$ alkyl group, preferably a methyl group.

8 Claims, No Drawings

POLYETHYLENE GLYCOL ESTERS OF POLYUNSATURATED FATTY ACIDS

The invention relates to polyethylene glycol esters of polyunsaturated fatty acids.

In many contexts polyunsaturated fatty acids are desirably made up as aqueous formulations that will be well tolerated in the body and will allow such acids to be well utilised especially in parental and topical applications. We have found that the use of polyethylene glycol esters of the fatty acids satisfies such requirements.

The invention thus provides, as nutritional, cosmetic or pharmaceutical formulations, polyethylene glycol esters in which the polyethylene glycol chain is terminated at one end by a polyunsaturated fatty acyl group preferably $C_{18}$–$C_{22}$ and at the other end by a straight or branched chain $C_1$–$C_4$ alkyl group, preferably a methyl group.

Such esters are desirably of formula.

$$A\text{—}(OCH_2CH_2)_n\text{—}O\text{—}A^1 \quad (1)$$

where A is the polyunsaturated fatty acyl group; $A^1$ is a straight or branched chain alkyl group as above; and n is an integer to give a molecular weight of 1,000D to 6,000D.

A variety of nutritionally or otherwise bioactive $C_{18}$–$C_{22}$ fatty acids with 2 to 6 unsaturations are known but the polyunsaturated fatty acids forming the present esters are preferably selected from the n-6 and n-3 essential fatty acids and most preferably the "delta 6-desaturated" acids that is to say the 18:3 n-6 and 18:4 n-3 and higher acids in the n-6 and n-3 series, particularly GLA, DGLA, AA, SA EPA and DHA. Their nomenclature and their conversions within biological systems are set out in table 1.

acids, desirably in all—cis form, but are not limited to them nor to acids in which the chain contains repeating —CH=CH—CH₂— units. Columbinic acid (CA) and α-parinaric acids (αPA) are other suitable acids and their formulae are. respectively e,z,z-octadeca-5,9,12-trienoic acid and z,e,e,z-octadeca-9,11,13,15-tetraenoic acid. A further suitable acid is α-eleostearic acid.

Compounds of type (1) may be synthesized by the reaction of terminally blocked polyethers of type RH, wherein R is a straight or branched chain $C_1$–$C_4$ alkyl terminated polyethylene glycol chain as referred to earlier i.e. —$(OCH_2CH_2)_n$—O—$A^1$, with derivatives of fatty acids e.g. of type A—O—A or A—X where X is Cl or Br. The reaction may for example be carried out in a suitable solvent such as toluene or acetone at temperatures between 0° C. and 150° C. with or without a suitable base e.g. anhydrous potassium carbonate.

Compounds of type (1) may also be synthesized by the reaction of the polyethers, RH with fatty acids of type A—OH. The reaction may for example be carried out with or without a suitable solvent such as toluene or xylene in the presence of a suitable acid e.g. p-toluenesulphonic acid at temperatures between 50° C. and 180° C. so that the water formed is removed from the reaction e.g. by azeotropy or under vacuum.

Alternatively, the reaction may for example be carried out in a suitable solvent such as dichloromethane in the presence of a condensing agent e.g. dicyclohexylcarbodiimide and in the presence of a strong non-nucleophilic base e.g. 4-dimethylaminopyridine at temperatures between 0° C. and 50° C.

Compounds of type (1) may further for example be synthesized by the reaction of polyethers, RH with fatty

TABLE 1

| n-6 EFA's | | n-3 EFA's |
|---|---|---|
| 18:2n-6 (Linoleic acid LA) | | 18:n-3 (α-Linolenic acid, ALA) |
| ↓ | delta-6-desaturase | ↓ |
| 18:3n-6 (γ-Linoienic acid GLA) | | 18:4n-3 (Stearidonic acid) |
| ↓ | elongation | ↓ |
| 20:3n-6 (Dihomo-γ-linoienic acid, DGLA) | | 20:4n-3 |
| ↓ | delta-5-desaturase | ↓ |
| 20:4n-6 (Arachidonic acid, AA) | | 20:5n-3 (Eicosapentaenoic acid, EPA) |
| ↓ | elongation | ↓ |
| 22:4n-6 (Adrenic acid, AdrA) | | 22:5n-3 |
| ↓ | delta-4-desaturase | |
| 22:5n-6 | | 22:6n-3 (Docosahexaenoic acid, DHA) |

The acids, which in nature are of the all—cis configuration, are systematically named as derivatives of the corresponding octadecanoic, eicosanoic or docosanoic acids, e.g. z,z-octadeca-9,12-dienoic acid or z,z,z,z,z,z-docosa-4,7,10,13,16,19-hexaenoic acid, but numerical designations based on the number of carbon atoms, the number of centres of unsaturation and the number of carbon atoms from the end of the chain to where the unsaturation begins, such as, correspondingly, 18:2 n-6 or 22:6 n-3, are convenient. Initials, e.g. EPA, and shortened forms of the name e.g. eicosapentaenoic acid, are used as trivial names in some instances.

The preferred polyethylene glycol esters are as stated derived from the above twelve n-6 and n-3 essential fatty acids of type A—OH or fatty acid esters of type A—O—Y, wherein Y is defined as an alkyl group containing a 1–4 carbon atoms which may be branched, unbranched, saturated or unsaturated e.g. vinyl, in the presence of a hydrolase enzyme with or without a suitable solvent e.g. toluene at temperatures between 20° C. and 80° C. such that the water or alcohol formed is removed from the reaction e.g. by molecular sieves or by vacuum.

Compounds of type (1) may still further be synthesized by the reaction of the polyethers. RH with fatty acid esters of type A—O—Y where Y is as above in the presence of a catalytic amount of an alcoholate of type $M^{30}OY^{31}$ where Y is as above and M is an alkali or alkaline earth metal e.g. sodium. The reaction is carried out with or without a suitable solvent eg. toluene at temperatures between 50° C. and 180° C. such that the lower alcohol, HO—Y formed is removed from the reaction mixture e.g. by azeotropy or by vacuum.

The compounds of type (1) are typically from 0.5–30% particularly 5–30% and more particularly 5–20% soluble in water at 25° C. and by analysis are shown to contain from 60–100% of the theoretical amount of fatty acyl groups. The solubility in water confers major formulation advantages on the fatty acids allowing them to be used for oral, parenteral, enteral or topical administration as solutions, emulsions, mixtures, creams, lotions or other delivery systems known to those skilled in the art.

SYNTHESIS EXAMPLES

Example 1

A mixture of polyethylene glycol-ω-methyl ether (RH, n=40–50, average MW=2,000) (1.0 wt) in toluene (15 vol) is distilled at atmospheric pressure until the volume of the remaining solution is 10 vol. This removes traces of water in the polyether. To the gently refluxing solution under a nitrogen blanket, is added z,z,z-octadeca-6,9,12-trienoyl chloride, GLA-Cl (0.296 wt) dropwise over 10–20 minutes and the mixture is heated under reflux for a further 15–20 minutes. After cooling, the solvent is removed in vacuo (40–60° C./20–40 mb) to give a gummy solid which is recrystallised from acetone (5–6 vol) by cooling the hot solution to 0–5° C. There is obtained α-(z,z,z-octadeca-6,9,12-trienoyl)-polyethylene glycol (av. MW=2000)-ω-methyl ether, [R(n=40–50)-GLA] m.p. 50–52.5° C. as an off-white crystalline solid.

Example 2

By proceeding in a similar manner but replacing the polyethylene glycol-ω-methyl ether (RH, n=40–50. average MW=2,000) with an equivalent amount of polyethylene glycol-ω-t-butyl ether (RH, n=40–50. average MW=2.000) there is prepared α-(z,z,z-octadeca-6,9,12-trienoyl)-polyethylene glycol (av. MW=2000)-ω-t-butyl ether. [R(n=40–50)-GLA], m.p. 48–53° C. as an off-white crystalline solid.

Example 3

By proceeding in a similar manner but replacing the GLA-Cl with an equivalent amount of z,z-octadeca-9,12-dienoyl chloride LA-Cl, there is prepared cc-(z,z-octadeca-9,12-dienoyl)-polyethylene glycol (av. MW=2000)-ω-methyl ether, [R(n=40–50)-LA], m.p. 52–53° C. as an off white crystalline solid.

Example 4

By proceeding in a similar manner but replacing the GLA-Cl with an equivalent amount of z,z,z,z,z-eicosa-5,8,11,14.17-pentaenoyl chloride, EPA-Cl, there is a prepared α-(z,z,z,z,z-eicosa-5,8,11,14,17-pentaenoyl)-polyethylene glycol (av. MW=2000)-ω-methyl ether, [R(n=40–50)-EPA] m.p. 51–53° C. as an off white crystalline solid.

Example 5

By proceeding in a similar manner but replacing the CLA-Cl with an equivalent amount of e,z,z,,-octadeca-5,9,12-trienoyl chloride, CA-Cl, there is a prepared α-(e,z,z,-octadeca-5,9,12 -trienoyl)-polyethylene glycol (av. MW=2,000)-ω-methyl ether, [R(n=40–50)-CA] m.p. 50–53° C. as an off white crystalline solid.

Example 6

By proceeding in a similar manner but replacing the GLA-Cl with an equivalent amount of z,z,z,-eicosa-8,11,14-trienoyl chloride, DGLA-Cl, there is a prepared α-(z,z,z,-eicosa-8,11,14,-trienoyl)-polyethylene glycol (av. MW=2000)-ω-methyl ether, [R(n=40–50)-DGLA] m.p. 50–53° C. as an off white crystalline solid.

Example 7

By proceeding in a similar manner but replacing the GLA-Cl with an equivalent amount of z,z,z,z,z,z-docosa-4,,10,13,16,19-hexaenoyl chloride, DHA-Cl, there is a prepared α-(z,z,z,z,z,z-docosa-4,7,10,13,16,-19-hexaenoyl)-polyethylene glycol (av. MW=2000)-ω-methyl ether, [R(n=40–50)-DHA] m.p. 48–50° C. as an off white crystalline solid.

Example 8

By proceeding in a similar manner but replacing the GLA-Cl with an equivalent amount of z,z,z,z,-eicosa-5,8,11,14,-tetraenoyl chloride. AA-Cl, there is a prepared α-(z,z,z,z,-eicosa-5,8,11,14,-tetraenoyl)-polyethylene glycol (av. MW-2000)-ω-methyl ether, [R(n40–50)-AA] m.p. 50–52° C. as an off white crystalline solid.

USE EXAMPLES

Example 9
Compositions for Intravenous Administration of Water-soluble Fatty Acids.

Polyethylene glycol esters as above containing linoleate, gamma-linolenate, dihomo-gamma-linolenate, arachnidonate, adrenate, docosapentaenoate, alpha-linolenate, stearidonate, eicosapentaenoate, docosahexaenoate, parinarate, alpha-eleostearate or other appropriate fatty acid derivative of the polyethylene glycol are made up at 5–300 mg/ml, preferably 50–200 mg/ml in an appropriate solution such as 100% water or a minimum amount of ethanol in water or 0.9% saline, in sterile ampoules. Such ampoules are added to appropriate conventional intravenous fluids for use.

Example 10
Topical Formulation

Following is an example of a skin cream containing polyethylene glycol esters of unsaturated fatty acids. together with evening primrose oil.

|  | % w/w |
| --- | --- |
| Evening Primrose Oil | 20% |
| Conventional Base Cream | 14% |
| Polyethylene glycol esters of unsaturated fatty acids (Examples 1–8) | 5% |
| Stabiliser | 2% |
| Preservative: |  |
| antioxidant (tocopherol) | 0.1 |
| antimicrobial | 0.2 |
| Water to 100% |  |

Example 11
Oral Formulations:
i) A soft or hard gelatin capsule containing 50–500mg of PEG esters of GLA or other unsaturated acids (Examples 1–8).

ii) A tablet or pastille containing 100–200 mg PEG esters as last.
iii) An oral emulsion or solution for external administration containing polyethylene glycol derivatives of unsaturated fatty acids as above, which have slightly emulsifying properties. The formulation is conventional apart from the polyethylene glycol derivative and is:

|  | % w/w |
| --- | --- |
| PEG ester | 40% |
| Emulsifier | |
| Preservative: | |
| antimicrobial | 0.2% |
| antioxidant (tocopherol) | 0.2% |
| Flavour | 0.1% |
| Water to 100% | |

What is claimed is:

1. A nutritional, cosmetic or pharmaceutical formulation which comprises at least one ester of polyethylene glycol in which the polyethylene glycol chain is terminated at one end by a polyunsaturated fatty acyl group and at the other end by a $C_1$–$C_4$ alkyl group and the ester is 0.5–30% soluble in water at 25° C.

2. The nutritional, cosmetic or pharmaceutical formulation of claim 1, wherein the ester of polyethylene glycol has the following formula

A—(OCHC$_2$CH$_2$)$_n$—O—A$^1$ wherein A is a polyunsaturated fatty acyl group; $A^1$ is a $C_1$–$C_4$ alkyl group; n is an integer to give a molecular weight of 1000 to 6000.

3. The nutritional, cosmetic or pharmaceutical formulation of claim 2, wherein A is a "delta-6-desaturated" essential fatty acyl group.

4. The nutritional, cosmetic or pharmaceutical formulation of claim 2, wherein A is a GLA, DGLA, AA, SA, EPA or DHA fatty acyl group.

5. The nutritional, cosmetic or pharmaceutical formulation of claim 2, wherein A is a columbinic or α-parnaric or α-eleostearic fatty acyl group.

6. The nutritional, cosmetic or pharmaceutical formulation of claim 2, wherein the polyunsaturated fatty acyl group is a $C_{18}$–$C_{22}$ acyl group.

7. The nutritional, cosmetic or pharmaceutical formulation of claim 2, wherein the $C_1$–$C_4$ alkyl group is a methyl group.

8. A method of releasing a fatty acid in a subject which comprises administering to the subject the nutritional, cosmetic or pharmaceutical formulation of claim 2 to the subject.

* * * * *